United States Patent [19]

Isenberg et al.

[11] 4,310,402

[45] Jan. 12, 1982

[54] GAS TIGHT SEALANT FOR ZIRCONIA SENSORS

[75] Inventors: Arnold O. Isenberg, Pittsburgh; David F. Bradley, McKeesport, both of Pa.

[73] Assignee: Westinghouse Electric Corp., Pittsburgh, Pa.

[21] Appl. No.: 204,144

[22] Filed: Nov. 5, 1980

Related U.S. Application Data

[63] Continuation of Ser. No. 93,650, Nov. 13, 1979, abandoned, which is a continuation of Ser. No. 4,258, Jan. 18, 1979, abandoned.

[51] Int. Cl.³ .............................................. G01N 27/58
[52] U.S. Cl. ................................... 204/195 S; 106/57; 106/62; 106/65; 106/73.2; 501/15; 501/105; 501/125; 501/134; 501/152
[58] Field of Search .............. 204/195 S, 1 S; 106/62, 106/57, 65, 73.2

[56] References Cited

U.S. PATENT DOCUMENTS

| | | | |
|---|---|---|---|
| 3,588,573 | 6/1971 | Chen et al. | 313/221 |
| 3,719,574 | 3/1973 | Richardson | 204/195 S |
| 3,776,831 | 12/1973 | Roy et al. | 204/195 S |
| 3,791,954 | 2/1974 | Noda et al. | 204/195 S |
| 3,904,486 | 9/1975 | Faurschou et al. | 204/1 T |
| 3,909,385 | 9/1975 | Spielberg et al. | 204/195 S |
| 3,935,089 | 1/1976 | Togawa et al. | 204/195 S |
| 3,964,918 | 6/1976 | Hares et al. | 106/47 Q |
| 4,035,277 | 7/1977 | Hennessy et al. | 204/195 S |
| 4,046,661 | 9/1977 | Stringer et al. | 204/195 S |
| 4,127,463 | 11/1978 | Rohr et al. | 204/195 S |

FOREIGN PATENT DOCUMENTS 1496319  10/1973  Fed. Rep. of Germany.

Primary Examiner—G. L. Kaplan
Attorney, Agent, or Firm—M. P. Lynch

[57] ABSTRACT

In a high temperature gas measuring device consisting of a zirconia oxide solid electrolyte cell bonded to a support member, a sealant exhibiting a thermal coefficient of expansion comparable to zirconia and a melting point in excess of 1000° C. is used to seal the cell to the support member. The preferred sealants which meet these requirements include:

(1) $3\,MgO\cdot Al_2O_3\cdot 6\,SiO_2$
(2) 52% $Nd_4(SiO_4)_3$, 48% $Ca_2SiO_4$
(3) 57% $La_4(SiO_4)_3$, 43% $Ca_2SiO_4$
(4) 50% $Y_4(SiO_4)_3$, 50% $Ca_2SiO_4$
(5) (a) $La_2O_3\cdot Al_2O_3$: 50 mol % of each (b) 40% $La_2O_3\cdot 60\%\,Al_2O_3$.

3 Claims, 3 Drawing Figures

GAS TIGHT SEALANT FOR ZIRCONIA SENSORS

This is a continuation of application Ser. No. 093,650, filed Nov. 13, 1979, which in turn was a continuation of Ser. No. 004,258, filed Jan. 18, 1979 and both now abandoned.

BACKGROUND OF THE INVENTION

Stabilized and partially stabilized zirconia in the form of a tubular or a disk-type solid electrolyte cell has found widespread use as a gas sensing and measuring device. In many applications the cell is bonded to a ceramic or metal support member. The requirement for operating the cell at temperatures in excess of 600° C. necessitates a sealant for bonding the cell to the support member which exhibits a thermal coefficient of expansion similar to that of zirconia and has a melting point in excess of about 1000° C.

SUMMARY OF THE INVENTION

There is disclosed herein with reference to the accompanying drawing a group of sealants which essentially match the thermal expansion characteristics of zirconia, i.e., $10.5 \times 10^{-6}$ cm/cm, °C., and maintain a gas-tight bond between a zirconia element and a support member at temperatures in excess of 600° C.

DESCRIPTION OF THE DRAWING

The invention will become more readily apparent from the following exemplary description in connection with the accompanying drawings in which.

DESCRIPTION OF THE PREFERRED EMBODIMENTS

Figure 1A:
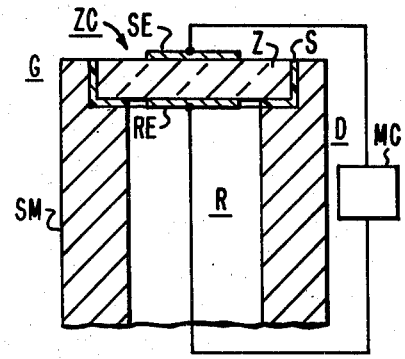
FIG. 1A and 1B are section schematic illustrations of gas measuring devices employing a zirconia solid electrolyte electrochemical cell bonded to a support member.
Figure 1B:
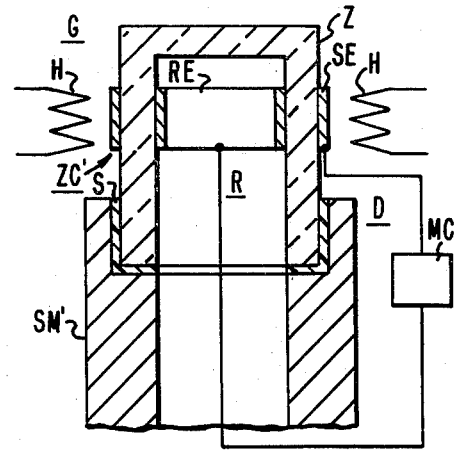

Typical implementations of gas measuring devices D consisting of a zirconia solid electrolyte electrochemical cell bonded to a support member by a sealant are illustrated in FIGS. 1A and 1B.

In the embodiment of FIG. 1A the zirconia cell ZC is a disk member bonded to the open end of a tubular support member SM, whereas the zirconia cell ZC' of FIG. 1B is a closed end tubular member sealed to the open end of a support member SM'. In both embodiments the stabilized zirconia cell consists of a zirconia solid electrolyte E having a sensing electrode SE disposed on one surface of the electrolyte E and a reference electrode RE disposed on the opposite surface. The sensing electrode SE is exposed to a monitored gas environment G having an unknown oxygen partial pressure. A stable oxygen environment is maintained in contact with the reference electrode RE such that the cell (ZC, ZC') will generate an electrical signal, as measured by the measuring circuit MC, which corresponds to the difference in oxygen partial pressure between the monitored gas environment G and the reference R. This measurement is indicative of the oxygen partial pressure of the monitored gas environment G.

Numerous compositions for formulating a zirconia, oxygen ion conductive solid electrolyte electrochemical cell are well known in the prior art. The more typical stabilizing materials are calcia and yttria. A detailed discussion of the electrolyte compositions and their operation as oxygen measuring elements is described in Feissue U.S. Pat. No. Re. 28,792 which is assigned to the assignee of the present invention and incorporated herein by reference. In order to establish optimum oxygen ion conductivity, the zirconia cell (ZC, ZC') must be operated at a temperature typically in excess of 600° C. While in some instances the temperature of the monitored gas environment G, as illustrated in FIG. 1, is sufficient to establish the desired zirconia cell operating temperature, a heater H, as illustrated in FIG. 1B, is often required to establish the desired operating temperature.

The accurate measurement of the oxygen partial pressure of the monitored gas environment G requires a gas-tight bond, via sealant S, to avoid gas leakage between the monitored gas environment G and the oxygen reference R. While numerous sealant compositions may adequately provide the desired gas-tight sealing at low temperatures, the requirement for operating the zirconia cell (ZC, ZC') at temperatures in excess of 600° C. places an additional stringent requirement on the sealant S to ensure the integrity of the seal between the cell (ZC, ZC') and the support member (SM, SM') at elevated temperatures. Thus, the sealant S must not only exhibit a thermal coefficient of expansion comparable to zirconia, i.e., $10.5 \times 10^{-6}$ cm/cm, °C., but it must have a melting point at a temperature in excess of 1000° C. and be chemically compatible with zirconia. While the material composition of the support members (SM, SM') of the embodiments of FIGS. 1A and 1B are illustrated to be metal, ceramic support members exhibiting thermal expansion characteristics similar to zirconia can be employed.

In an effort to identify preferred sealant compositions which exhibit compatible thermal expansion characteristics and provide gas-tight bonding of the zirconia cell (ZC, ZC') to the support member (SM, SM') at temperatures in excess of 600° C., a large number of mixed oxide systems were selected from phase diagrams on the basis of melting point and chemical composition characteristics that would be compatible with zirconia. Oxide mixtures with electronic and ionic conduction were excluded as possible candidates. Mixtures were pressed and sintered into bars for thermal expansion measurements and melting points were determined by the compression of candidate materials at increasing temperatures between zirconia plates. Sealants containing transition metal oxides and titania were unacceptable due to their adverse interaction with zirconia at high temperatures. This evaluation process produced several sealant compositions exhibiting melting points in excess of 1000° C. and thermal coefficients of expansion that were sufficiently close to that of zirconia to produce the desired gas-tight seal. The preferred sealant compositions for bonding zirconia to support members are:

| | | |
|---|---|---|
| (1) $3 MgO \cdot Al_2O_3 \cdot 6 SiO_2$ | | Thermal Expansion $9.8 \times 10^{-6}$ cm/cm,°C. |
| (2) 52% $Nd_4(SiO_4)_3$, 48% $Ca_2SiO_4$ | | Thermal Expansion $10.8 \times 10^{-6}$ cm/cm, °C. |
| (3) 57% $La_4(SiO_4)_3$, 43% $Ca_2SiO_4$ | | Thermal Expansion $11 \times 10^{-6}$ cm/cm, °C. |
| (4) 50% $Y_4(SiO_4)_3$: 50% $Ca_2SiO_4$ | | Thermal Expansion $11.1 \times 10^{-6}$ cm/cm, °C. |
| (5) (a) $La_2O_3Al_2O_3$: 50 mol % each | | Thermal Expansion $10 \times 10^{-6}$ cm/cm, °C. |

| |
|---|
| (b) 40 mol % $La_2O_3$ . 60 mol % $Al_2O_3$ |

Items (2), (3) and (4) are selected rare earth oxides, i.e., neodymium, lanthanum, and yttrium in combination with $CaO + SiO_2$.

Figure 2:
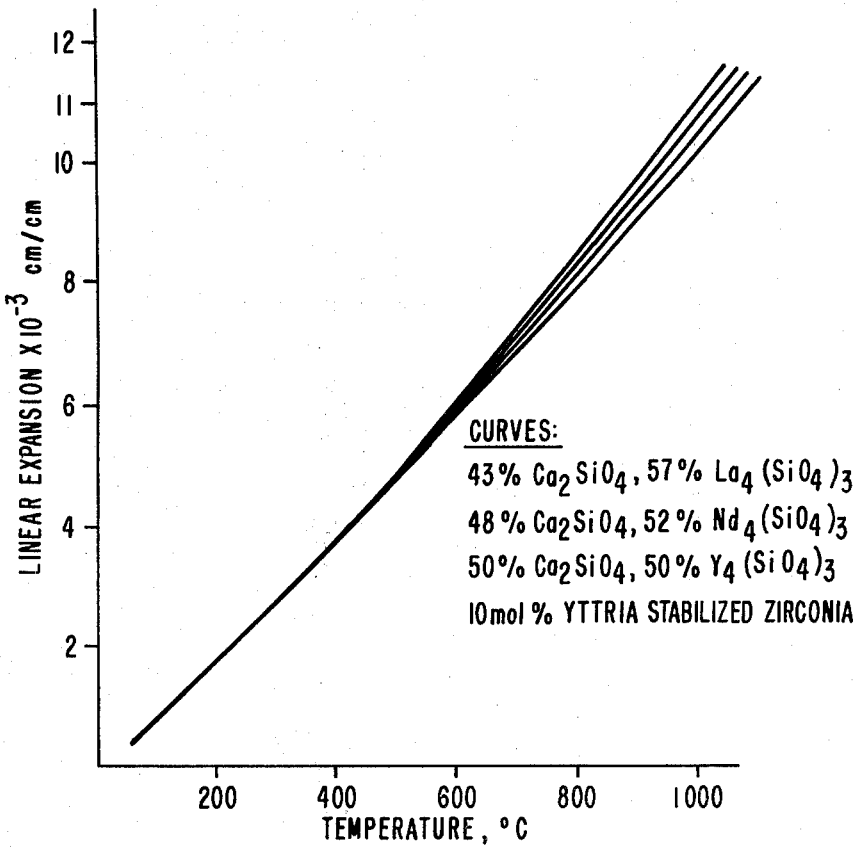
FIG. 2 is a graphical illustration of the thermal expansion characteristics of preferred sealants as compared to the thermal expansion characteristics of zirconia.

The thermal expansion characteristics of yttria stabilized zirconia and that of the three sealant compositions (2), (3) and (4) of mixtures of silicates and oxides are graphically illustrated in FIG. 2. As is apparent from the data of FIG. 2 which was derived through actual temperature cycling of the compositions noted on FIG. 2, an extremely close match of thermal expansion characteristics of the three sealant compositions and the yttria stabilized zirconia is achieved.

It has been determined experimentally that variations in the above compositions which retain a composition thermal coefficient of expansion of ±10% of the thermal coefficient of expansion of zirconia are acceptable.

We claim:

1. In a gas-sensing apparatus having a zirconia solid electrolyte electrochemical cell sealed to a support member for measuring a gas constituent of interest at a temperature of approximately 600° C. or higher, the combination of:
   a support member having a coefficient of thermal expansion approximating that of zirconia, and
   a sealant composition having a coefficient of thermal expansion which is within a range of ±10% of the coefficient of thermal expansion of zirconia and a melting point at a temperature in excess of 1000° C., for sealing said zirconia solid electrolyte electrochemical cell to said support member, said sealant composition being selected from the following formulations:
   (a) $La_2O_3.Al_2O_3$: approximately 50 mol% of each
   (b) 40% $La_2O_3$.60% $Al_2O_3$.

2. In a gas-sensing apparatus having a zirconia solid electrolyte electrochemical cell sealed to a support member for measuring a gas constituent of interest at a temperature of 600° C. or higher, the combination of:
   a support member having a coefficient of thermal expansion approximating that of zirconia,
   a sealant composition having a coefficient of thermal expansion which is within a range of ±10% of the coefficient of thermal expansion of zirconia and a melting point at a temperature in excess of 1000° C. to seal said zirconia solid electrolyte electrochemical cell to said support member, said sealant composition consisting of a mixture of a rare earth oxide selected from the group consisting of neodymium oxide, lanthanum oxide and yttrium oxide, 3. In a gas-sensing apparatus having a zirconia solid electrolyte electrochemical cell sealed to a support member for measuring a gas constituent of interest at a temperature of approximately 600° C. or higher, the combination of:
   a support member having a coefficient of thermal expansion approximating that of zirconia, and
   a sealant composition of silicates and rare earth element oxides having a coefficient of thermal expansion which is within a range of ±10% of the coefficient of thermal expansion of zirconia and a melting point at a temperature in excess of 1000° C. for sealing said zirconia solid electrolyte electrochemical cell to said support member.

* * * * *